US011389581B1

(12) United States Patent
Orth

(10) Patent No.: US 11,389,581 B1
(45) Date of Patent: Jul. 19, 2022

(54) BLOOD PROCESSING APPARATUS AND METHOD FOR PREVENTING CANCER METASTASIS

(71) Applicant: Orth Consulting, LLC, Maineville, OH (US)

(72) Inventor: Donald S. Orth, Cincinnati, OH (US)

(73) Assignee: ORTH CONSULTING, LLC, Maineville, OH (US)

( * ) Notice: Subject to any disclaimer, the term of this patent is extended or adjusted under 35 U.S.C. 154(b) by 0 days.

(21) Appl. No.: 17/362,470

(22) Filed: Jun. 29, 2021

(51) Int. Cl.
*A61M 1/36* (2006.01)
*A61M 1/26* (2006.01)
(Continued)

(52) U.S. Cl.
CPC .............. *A61M 1/3687* (2013.01); *A61K 8/66* (2013.01); *A61M 1/267* (2014.02); *A61M 1/36* (2013.01); *A61M 1/3618* (2014.02); *A61M 1/3621* (2013.01); *A61M 1/3679* (2013.01); *A61M 1/3689* (2014.02); *B01D 63/02* (2013.01); *B01D 63/06* (2013.01); *B01D 69/04* (2013.01); *B01D 69/08* (2013.01); *B01J 31/00* (2013.01); *B01J 31/003* (2013.01); *C12N 11/00* (2013.01); *C12N 11/02* (2013.01); *C12N 11/06* (2013.01); *C12N 11/14* (2013.01); *C12N 11/16* (2013.01); *A61M 2202/0445* (2013.01); *A61M 2205/3303* (2013.01); *A61M 2205/3368* (2013.01)

(58) Field of Classification Search
CPC ...... A61M 1/267; A61M 1/36; A61M 1/3618; A61M 1/3621; A61M 1/3687; A61M 1/3689; A61M 1/3679; A61M 2202/0445; A61M 2205/3368; A61M 2205/3303; A61M 2205/336; B01D 63/02; B01D 63/06; B01D 69/04; B01D 69/08; C12N 11/00; C12N 11/02; C12N 11/06; C12N 11/14; C12N 11/16; B01J 31/00; B01J 31/003; A61K 8/66
See application file for complete search history.

(56) References Cited

U.S. PATENT DOCUMENTS 3,849,254 A * 11/1974 Kirwan ..................... C09K 3/30
435/176
4,356,267 A * 10/1982 Callegaro ........... A61M 1/3679
210/321.89

(Continued)

OTHER PUBLICATIONS https://www.prospecbio.com/dnase_i_human?gclid=EAIaIQobChMItJ H25Y_18gIVCZflCh05lgSnEAMYASAAEgKx3fD_BwE ProSpec Brochure (2016).*

(Continued)

*Primary Examiner* — John Kim
(74) *Attorney, Agent, or Firm* — David R. Stevens; Stevens Law Group

(57) ABSTRACT

A blood treatment method includes the steps of inducing flow of a patient's blood through an extracorporeal device inlet and outlet in fluid connection to the circulatory system of the patient. Metastatic DNA contained within patient blood can be rendered non-oncogenic by passing patient blood over a biochemical reactor surface having attached or immobilized DNase 1 enzyme, with the biochemical reactor being contained within the extracorporeal device. The treatment method is performed without adding any chemicals to the blood of the patient.

24 Claims, 7 Drawing Sheets

(51) Int. Cl.

| | |
|---|---|
| *A61K 8/66* | (2006.01) |
| *C12N 11/02* | (2006.01) |
| *B01J 31/00* | (2006.01) |
| *C12N 11/14* | (2006.01) |
| *C12N 11/16* | (2006.01) |
| *C12N 11/00* | (2006.01) |
| *B01D 63/02* | (2006.01) |
| *B01D 69/04* | (2006.01) |
| *B01D 69/08* | (2006.01) |
| *B01D 63/06* | (2006.01) |
| *C12N 11/06* | (2006.01) |

(56) References Cited

U.S. PATENT DOCUMENTS

| | | |
|---|---|---|
| 10,881,781 B1 | 1/2021 | Orth |
| 2015/0166978 A1* | 6/2015 | Cooney ............... A61M 1/3496 422/44 |
| 2015/0246170 A1* | 9/2015 | Miao ................... A61M 1/3679 210/663 |

OTHER PUBLICATIONS

Alcazar-Leyva et al., Med Sci Monit, 15 (2), CR51-55 (2019).*
Hawes et al., Cancer Research, 75(20), pp. 4260-4264 (2015).*
Massague, J, E. Batlle and R.R. Gomis, Understanding the molecular mechanisms driving metastasis, Molecular Oncology 11:3-4 (2017).
Garcia-Olmo, G. et al., Horizontal transfer of DNA and the "genometastasis hypothesis", Blood 95(2):724-725 (2000).
Thierry, A.R. et al., Origins, structures, and functions of circulating DNA in oncology, Cancer Metastasis Rev. 35:347-376 (2016).
Garcia-Olmo, G. et al., Quantitation of cell-free DNA and RNA in plasma during tumor progression in rats, Molecular Cancer 12(8):1-10 (2013).
Lo, K.W., et al., Analysis of cell-free Epstein-Barr virus associated RNA in the plasma of patients with nasopharyngeal carcinoma, Clin. Chem. 45:1292-1294 (1999).
Kopreski, M.S., et al., Detection of tumor messenger RNA in the serum of patients with malignant melanoma, Clin. Cancer. Res. 5:1961-1965 (1999).
Alekseeva, L.A., et al., Targeting circulating SINEs and LINES with DNase 1 provides metastases inhibition in experimental tumor models, Molecular Therapy: Nucleic Acids 20:50-61 (2020).
Patulina, O.A. et al., Tumoricidal activity of RNase and DNase 1. Acta Naturare 2 No. 1(4):88-93 (2010).
Tamkovich, S.N., et al., Circulating DNA and DNase activity in human blood, Ann. N.Y. Acad. Sci. 1075:191-196 (2006).
Fleischhacker, M. and B. Schmidt, Pre-analytical issues in liquid biopsy—where do we stand? J. Lab Med. 44(3):117-142 (2020).
Park, J., et al., Cancer cells induce metastasis-supporting neutrophil extracellular DNA traps, Sci. Transl. Med. 8:(361ra138), 1-12 (2016).
Kolaczkowska, E., et al. Molecular mechanisms of NET formation degradation revealed by intravital imaging in the liver vasculature, Nat. Commun. 6(6673):1-13 (2015).
Cools-Lartigue, J., et al., Neutrophil extracellular traps sequester circulating tumor cells and promote metastasis, J. Clin. Invest. 123:3446-3458 (2013).
Tohme, S., et al., Neutrophil extracellular traps promote the development and progression of liver metastases after surgical stress, Cancer Res. 76:1367-1380 (2016).
Yang, L., et al. DNA of neutrophil extracellular traps promotes cancer metastasis via CCDC25, Nature 583(7814): 133-138 (2020).

* cited by examiner

BLOOD PROCESSING APPARATUS AND METHOD FOR PREVENTING CANCER METASTASIS

FIELD OF THE INVENTION

This invention relates to preventing metastasis of cancer from a primary tumor to other sites in a patient's body by enzymatic destruction of metastatic deoxyribonucleic acid (DNA) in a patient's bloodstream. More particularly, an extracorporeal biochemical reactor containing immobilized deoxyribonuclease 1 (DNase1) for enzymatic treatment of the blood of a cancer patient is described.

BACKGROUND OF THE INVENTION

Cancer may be viewed as an abnormal growth of cells that have lost the ability to stop growing. Cancers can occur almost anywhere in the body. Metastasis is the process by which cancer spreads to different sites in the body, and the majority of deaths due to cancer are due to metastasis of the original tumor cells to organs distant from the original or primary tumor rather than a consequence of the primary tumor (1). Garcia-Olmo, et al. (2) proposed the *Genometastasis Hypothesis* to describe metastases that might occur via transfection of susceptible cells located in distant target organs with dominant oncogenes that are derived from the primary tumor and are circulating in the blood. Such oncogenes may be present in cells or in cell-free, circulating DNA (cirDNA) that has been released from the primary tumor into the bloodstream.

The cirDNA may include both nuclear and/or mitochondrial DNA. Thierry et al. (3) noted that cirDNA is composed of many "kinds" of DNA depending on mechanisms of origin including apoptosis, necrosis, active release, phagocytosis, and exocytosis, and structural forms of cirDNA depend on the mechanism of release including particulate structures (exosomes, microparticles, apoptotic bodies) or macromolecular structures (nucleosomes, DNA traps, and complexes with serum proteins or cell-free membrane constituents). There is a basal amount of non-metastatic cirDNA found in the blood of healthy individuals, which indicates that normal, non-tumor cells release DNA into the circulation; however, it has been demonstrated that the amount of cirDNA in the bloodstream increases with increases in tumor cell number (3).

Furthermore, more elevated levels of cirDNA are found in the blood from advanced and metastatic cancer patients than in early stage cancer patients. These elevated levels are due to release from cancer cells because the basal cirDNA levels from normal cells remain constant (3). Garcia-Olmo et al. (4) reported that there was a large amount of non-tumor DNA released during all stages of tumor progression in rats, particularly in the early stages, which led them to believe that active interactions occur between tumor and non-tumor cells that are associated with the release of DNA during tumorigenesis. In addition, cell-free ribonucleic acid (RNA) was found in the plasma of cancer patients in various types of cancer including malignant melanoma, breast cancer, colorectal cancer and gastric cancer (4,5,6).

Alekseeva et al. (7) noted that cirDNAs play important roles at different stages of tumor progression and that DNase 1 inhibits metastasis in experimental tumor models. Patulina et al. (8) studied the antitumor and antimetastatic activities of RNase A and DNase 1 in two murine models: Lewis lung carcinoma and hepatoma A-1 metastasizing to the liver. They found that intramuscular (IM) administration of either RNase A or DNase 1 led to a two- to three-fold decrease in the number of metastases in the lungs or a decrease in the hepatic index (HI), which was calculated by dividing the liver weight by the body weight×100%. They found that IM administration of RNase A (0.35-7 µg/kg) or DNase 1 (0.02-2.3 mg/kg) resulted in considerable decrease in the metastasis number in the lung study and the HI in the liver study. They concluded that RNase A and DNase 1 are highly promising as supplementary therapy for the treatment of metastasizing tumors.

Tamkovich et al. (9) studied cirDNA and DNase activity in the blood plasma of healthy donors and patients with stomach or colon cancers. The average concentration of cirDNA in the plasma of healthy persons was 34±34 ng/ml and was accompanied with high DNase activity (0.356±0.410 ng/ml); whereas, the cirDNA level in plasma of patients with stomach and colon cancer was increased and the DNase levels were below the detection limits of their assay. Tamkovich and co-workers demonstrated that low DNase activity in blood plasma of cancer patients can cause an increase in the concentration of cirDNA. However, DNase activity in the blood depends on the concentration of DNase and the presence of inhibitors, such as actin, which forms an inactive 1:1 stoichiometric complex with DNase (9). These workers found that 0.005 U of added DNase was inhibited by 5 µl of blood plasma from cancer patients, and they concluded that inhibitors of DNase activity can account for the decreased activity of this enzyme in the blood of gastrointestinal cancer patients. Fleischhacker and Schmidt (10) observed that chemotherapy-induced toxicity, which is thought to cause the release of cell-free chromatin from dying cells which induces DNA damage, apoptosis, and inflammation in healthy bystander cells. They indicated that neutralization or degrading cell-free chromatin led to a decrease in inflammatory cytokines, apoptosis and inflammation. The release of actin, or other DNase-inhibiting compounds from apoptotic or necrotic cells, may inhibit normal physiological levels of DNase in the bloodstream and aid the metastasis of cancer to distant sites in the body, so it appears that adding DNase and/or inhibitors of actin to the bloodstream may help prevent metastases.

Neutrophils may kill harmful microorganisms by phagocytosis, by degranulation of cytotoxic enzymes into the extracellular space, and by neutrophil extracellular traps (NETs). Upon activation, neutrophils form NETs—meshes of DNA with cytotoxic enzymes (e.g., neutrophil elastase, cathepsin G, myeloperoxidase) that are released extracellularly to trap and kill infecting microorganisms. NETs may form in tissues or in the intravascular space (11). Intravascular NETs may damage vascular cells, and NETs induced within the vasculature by experimentally induced bacterial infection or surgical stress was found to aid metastatic seeding of cancer cells in the liver (11-14).

In 2016, Tohme et al. (14) reported that surgical stress resulted in formation of NETs that promoted the development and progression of liver metastases. They noted that liver resection is the only available treatment that offers a significant chance of cure for patients with metastatic colorectal cancer; however, surgical removal of malignancies often enhances the risk of tumor recurrence. Tohme and co-workers found that surgical stress was associated with a substantial increase in hepatic metastatic disease and that both DNase and inhibition of peptidyl arginine deiminase type IV (PAD4), an enzyme required for NET formation, alleviated metastases due to reduced formation of NETs, with resulting reduced NET-induced inflammatory mediator storms caused by surgical stress, which produced favorable oncologic outcomes in mice. These workers also noted that Toll-like receptors (TLRs) play a key role in the innate immune response to stress, that TLR9 is a cellular DNA receptor that is widely expressed in different cancers, and that it promotes tumor growth by activating a cascade of intracellular signaling pathways. Their work highlighted the value of DNase as a possible therapeutic option to help prevent metastases of cancer, especially after surgery, and possibly following infections.

Cools-Lartigue et al. (13) noted that manipulation of primary tumors during surgery is associated with increased numbers of circulating tumor cells. They observed that postsurgical infections may occur in up to 40% of some types of cancers, that severe infections often are associated with adverse oncological outcomes, and that elevated numbers of circulating neutrophils are correlated with adverse outcomes in patients with cancer. These workers demonstrated that cancer cells can become trapped within NETs, and this tumor cell entrapment within NETs promoted stable retention that permitted tumor invasion and growth in the liver and lungs of experimental animals. They also found that NETs were responsible for enhanced tumor cell migration and invasion in vitro, and they reported that invasion of liver cells was abrogated by the addition of 1,000 U DNase 1 or 5 µM neutrophil elastase inhibitor (NEi). They proposed that NETs were potential therapeutic targets in selected patients with cancer.

Park et al. (11) reported that metastatic breast cancer cells can induce neutrophils to form metastasis-supporting NETs in the absence of infection and that that treatment with DNase 1-coated nanoparticles reduced lung metastases in mice. They also proposed that induction of NETs by cancer cells is a potential therapeutic target.

NETs may also be formed in response to tissue inflammation, and it has been reported that NETs are associated with cancer metastasis in mouse models. Yang et al. (15) studied the clinical importance of NETs in cancer patients and found that NETs were present in relatively low numbers in primary tumors, but they were abundant in several metastatic lesions including those in the liver, lungs, bone, and brain. These workers found that serum NETs can predict the occurrence of liver metastases in patients with early stage breast cancer.

Interestingly, they found that NET-DNA acted as a chemotactic factor to attract cancer cells, rather than merely trapping metastatic cancer cells in mouse models, and they identified the transmembrane protein CCDC25 as the NET-DNA receptor that senses DNA to activate the integrin-linked kinase-beta (ILK-β) pathway to enhance cell motility. They demonstrated that NET-mediated metastasis is abrogated in CCDC25-knockout cells and with DNase 1—an endonuclease that degrades NET-DNA. These studies suggest that therapeutic treatment of cancer patients with DNase 1 and NEi or alpha-1 antitrypsin inhibitor (A1AT) to neutralize elastase may destroy cirDNA, disrupt NETs, and inhibit proteolytic action of neutrophil elastase to help prevent metastases and improve clinical outcomes, reduce morbidity, and save lives.

The above discussion indicates that cancer metastases may be influenced by factors that were unknown several years ago. Specifically, surgical procedures, microbial infections including sepsis, and chemotherapy that cause tissue damage may result in the release of cirDNA from tumor cells and recruitment of neutrophils that release NETs that form NET-DNA which may attract cancer cells, facilitate their metastasis by transmission to distant sites in the body via the bloodstream, and aid invasion of the cancer cells into susceptible host cells. Prophylactic treatment with DNase to prevent cirDNA and NET-DNA from metastasizing should be considered; however, Park et al. (11) noted that DNase had a short half-life in blood, which means that therapeutic use of DNase by conventional means (e.g., intravenous injection/infusion) may require repeated injections/continuous infusion and repetitive blood sampling and testing to maintain DNase in the desired therapeutic range, which may make this type of treatment impractical.

BRIEF SUMMARY OF THE INVENTION

This disclosure describes a system, apparatus and method that can accomplish therapeutic removal of selected nucleic acids within a biological system, including but not limited to those produced by cancer cells in humans and animals, and more specifically, removal of cancer metastases including cirDNA and NET-DNA in the blood of a patient by continuous passage of the blood of the patient through an extracorporeal biochemical reactor containing, but not limited to, nuclease enzymes, such as DNase 1, and returning the treated blood to the patient.

This extracorporeal treatment of the blood of a patient may be performed as a stand-alone procedure using DNase 1 in the biochemical reactor so that cirDNA and NET-DNA may be broken into non-cancerous DNA fragments as a result of action of DNase 1, with DNase 1 and other blood treatment elements including immobilized anti-actin to prevent its inhibition of DNase, immobilized RNase A or nuclease enzymes, immobilized phosphatases including *Saccharomyces boulardii* alkaline phosphatase (SBAP) or apyrase so metastatic nucleic acids and phosphorylated compounds in the blood of a patient can be broken down into non-cancerous DNA and/or RNA fragments and dephosphorylated as a result of action of the SBAP and/or other phosphatase enzymes (16) so that the cirDNA and DNA fragments are unable to attach to cellular recognition sites, such as TLRs, or the extracorporeal treatment of a patient's blood may be performed using immobilized DNase 1 in one biochemical reactor in a series of biochemical reactors, including immobilized anti-actin to prevent actin inhibition of DNase, immobilized RNase A or nuclease enzymes, immobilized phosphatases including SBAP or apyrase so these metastatic nucleic acids and phosphorylated compounds in the blood of a patient including DNA, RNA, ATP, and ADP, can be broken down into non-cancerous DNA, RNA and nucleotide fragments and dephosphorylated as a result of action of the SBAP and/or related phosphatase enzymes, so that the cirDNA and DNA fragments are unable to attach to cellular recognition sites, such as TLRs, immobilized monoclonal antibodies directed against actin (e.g., anti-actin), immobilized A1AT which would help neutralize neutrophil elastase in the manner described above for NEI by Cools-Lartigue et al. (13), and inhibition of PAD4 to help prevent NET formation, along with other forms of cancer treatment needed by a patient. The method described herein is superior to current therapies for treating cancer metastases that involve intravenous (IV) administration of chemicals that block cellular receptor sites for cirDNA, including CCDC25 and TLR9, monoclonal antibodies directed at cancer DNA which may become less effective over time as binding sites become saturated with target ligands, or IV administration of DNase 1 enzymes which may require repeated injections along with repetitive sampling and testing of a patient's blood to maintain proper therapeutic levels of these chemicals. Furthermore, immobilization of enzymes generally improves enzyme stability, so immobilized DNase 1 may have a longer half-life in the blood of a patient than IV administration of the same amount of DNase 1.

Treatment of the blood of a patient with the blood treatment apparatus and method described herein may be done without addition of any chemicals to the blood of the patient—no antibiotics, chemotherapeutic agents, hydrolytic enzymes, anti-coagulants such as heparin or sodium citrate, or anti-inflammatory agents—which eliminates the need for continuous injections/infusion of DNase 1, repetitive sampling of the patient's blood, and testing to determine if levels of the added DNase 1 are within the proper therapeutic range to prevent metastasis of tumor DNA.

In one embodiment, a blood treatment method includes the steps of inducing flow of patient blood through an extracorporeal device inlet and outlet in fluid connection to a circulatory system of a patient. Metastatic cirDNA and NET-DNA contained within patient blood can be rendered non-oncogenic by passing a patient's blood over a biochemical reactor surface having attached or immobilized endonuclease enzymes, with the biochemical reactor being contained within the extracorporeal device.

In one embodiment, the endonuclease is DNase 1. The DNase 1 hydrolyzes at least one of metastatic cirDNA, NET-DNA, and cirDNA complexed with serum proteins or cell-free membrane constituents in the blood of a patient, thereby hydrolyzing metastatic DNA to form DNA fragments that are not carcinogenic In one embodiment, the immobilized DNase 1 in the biochemical reactor destroys metastatic DNA contained within the blood of a patient by catalyzing the hydrolytic cleavage of phosphodiester linkages in the DNA backbone, thus degrading DNA and preventing metastasis from the primary tumor to other sites in the body.

In one embodiment, the immobilized DNase 1 and immobilized RNase A in the biochemical reactor, singly or in series, destroy metastatic cirDNA and metastatic circulating RNA (cirRNA) contained within the blood of a patient by catalyzing the hydrolytic cleavage of phosphodiester linkages in the DNA backbone and RNA backbone, respectively, thus degrading cirDNA and cirRNA and preventing metastases from the primary tumor to other sites in the body.

In one embodiment, the immobilized DNase 1 and immobilized monoclonal antibodies against actin (e.g., anti-actin) in the biochemical reactor, singly or in series, destroy metastatic cirDNA and NET-DNA contained within the blood of a patient by catalyzing the hydrolytic cleavage of phosphodiester linkages in the DNA backbone, thus degrading metastatic DNA and preventing metastasis from the primary tumor to other sites in the body, and the monoclonal anti-actin antibodies bind to actin to prevent it from interfering with DNase 1 activity.

In one embodiment, nuclease enzymes including DNase 1 are used to destroy metastatic cirDNA in the bloodstream of a patient to therapeutically treat at least one of brain cancer (such as glioblastoma), nerve cancer (such as Schwannomas and neurofibrosarcoma), sarcomas that develop from connective tissues including muscle, fat, and blood vessels, breast cancer, lung cancer, bone cancer, liver cancer, esophageal cancer, pancreatic cancer, stomach cancer, intestinal cancer, colorectal cancer, kidney cancer, bladder cancer, prostate cancer, uterine cancer, testis cancer, ovarian cancer, cardiac cancer, and skin cancers including malignant melanoma.

In one embodiment, DNase 1 enzyme is immobilized by being covalently attached to the biochemical reactor surface.

In one embodiment, the biochemical reactor surface of the extracorporeal blood processing apparatus further comprises at least one of capillary tubing and microbeads.

In one embodiment, a patient's blood can be pumped through an extracorporeal device inlet and outlet in fluid connection to the circulatory system of the patient.

In one embodiment, the biochemical reactor surface is provided with a continuous blood flow from the patient that continues until the metastatic cirDNA and NET-DNA being hydrolyzed have been reduced to predetermined or undetectable levels.

In one embodiment, a blood treatment system includes an extracorporeal device having an inlet and outlet able to be placed in in fluid connection to the circulatory system of a patient. A biochemical reactor surface having attached DNase 1 enzyme can act to hydrolyze cirDNA contained within patient blood. The biochemical reactor can be contained within the extracorporeal device.

BRIEF DESCRIPTION OF THE DRAWINGS

Embodiments will be readily understood by the following detailed description in conjunction with the accompanying drawings.

DETAILED DESCRIPTION OF THE INVENTION

This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, the term "about", when used in reference to numerical ranges, cutoffs, or specific values, is used to indicate that the recited values may vary by up to as much as 10% from the listed value. As many of the numerical values used herein are experimentally determined, it should be understood by those skilled in the art that such determinations can, and often times, will vary among different experiments. The values used herein should not be considered unduly limiting by virtue of this inherent variation. The term "about" is used to encompass variations of this sort up to, or equaling, 10%.

The term "attach," "attached" or "attachment" as used herein, refers to connecting or uniting by a chemical bond, link, or force in order to keep two or more chemical compounds, polymers, proteins, polysaccharides, lipids, nucleic acids, or other biological or manufactured compositions together.

As used herein, "for example," "for instance," "such as," or "including" are meant to introduce examples that further clarify a more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

Disclosed herein is an extracorporeal device, system or methods involving circulating, perfusing, or otherwise passing blood or other patient fluids through a system and device external to the body. One or more internal surfaces of the external or extracorporeal system include immobilized enzymatic agents to interact with one or more patient fluid borne biologic agents. The extracorporeal device, system or methods provide a platform that can be applied to numerous types of cancer to hydrolyze cirDNA and disrupt metastasis to prevent the spread of cancer from the primary tumor to other sites in the body.

Figure 1:
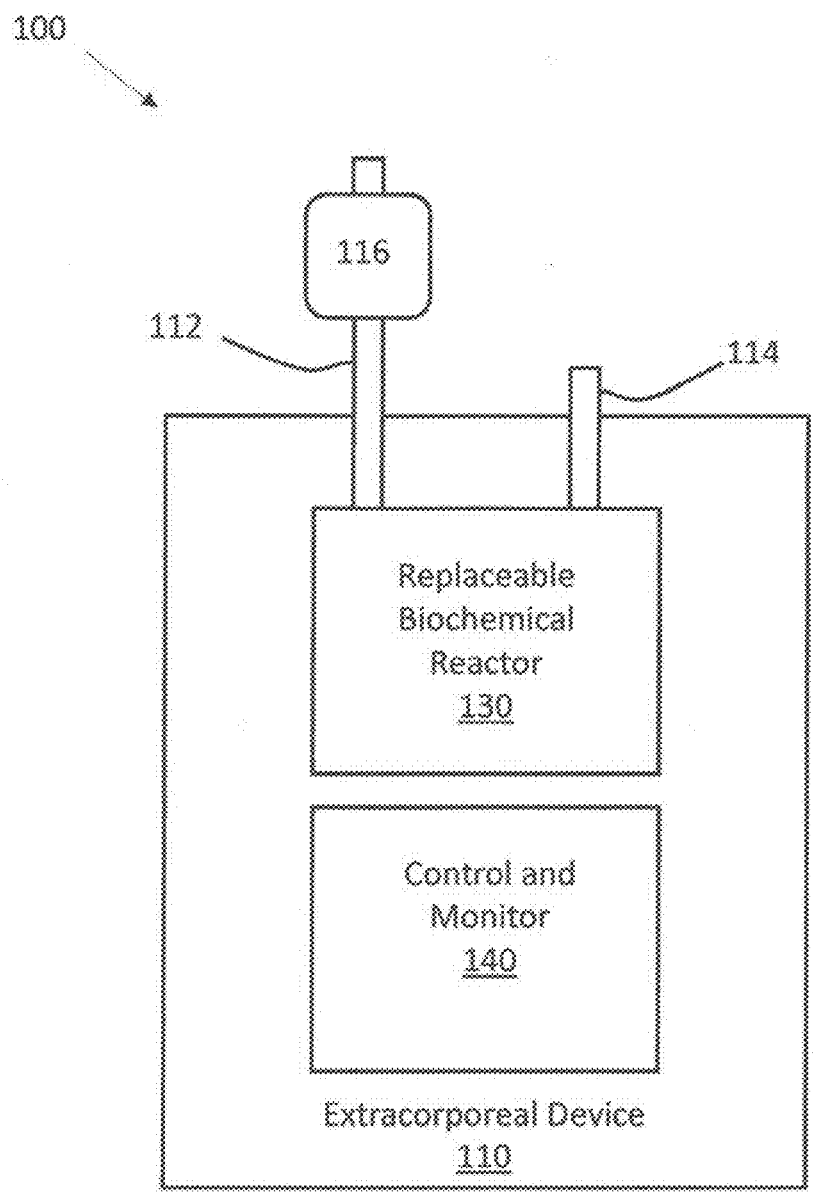
FIG. 1 illustrates a system including extracorporeal devices that can be attached to receive and treat blood or other fluids from a patient to prevent metastases.

FIG. 1 illustrates a system 100 that can be attached to receive blood or other fluids from a human or animal patient. The system 100 includes an extracorporeal device 110 having an inlet 112 and outlet 114. Using a fluid pump 116, blood or other fluid is introduced and passed through a replaceable biochemical reactor 130. In some embodiments, the biochemical reactor 130 can form the entirety of the extracorporeal device 110. Surface attached and immobilized enzymatic agents in the biochemical reactor can hydrolyze cirDNA in the blood and the processed blood may be returned to the patient using outlet 114. A control and monitoring system 140 can be used to set fluid flow rates, maintain, and monitor fluid temperature, and support sensors that can determine efficacy of cirDNA destruction.

Figure 2:
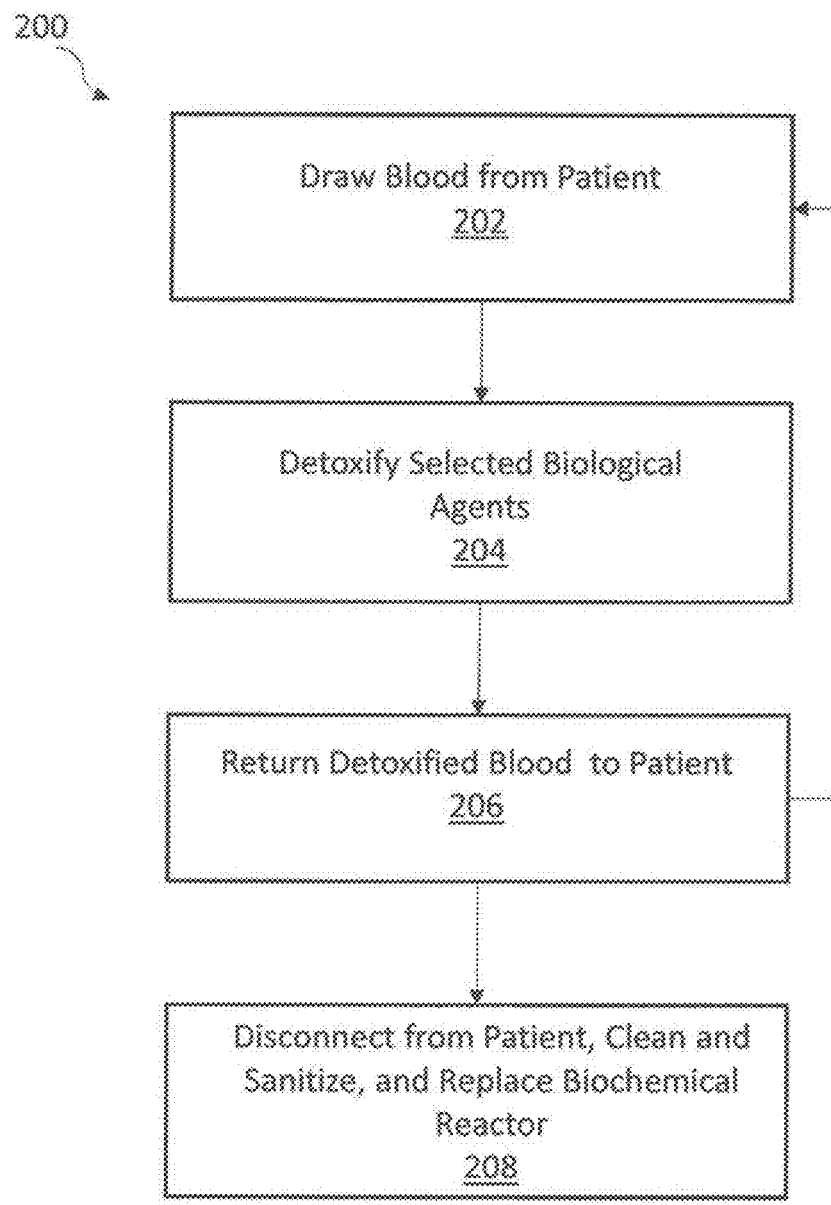
FIG. 2 illustrates one embodiment of a method for treating patient blood.

FIG. 2 illustrates one embodiment of a method 200 for treating human or animal patient blood. In a step 202, blood is drawn from a human or animal patient using a needle and suitable arterial or venous tap or puncture and transferred into an extracorporeal device. The cirDNA in the patient blood is hydrolyzed in step 204, and the process is intermittently or continuously repeated until all of patient blood has been processed and returned to the patient (step 206). This process may need to be continued until the primary tumor is eliminated, which may require surgical removal or killing of the tumor cells by irradiation or chemotherapy, with further DNase 1 treatment to insure complete destruction of the metastatic cirDNA in the blood of the patient. Then, the patient can be disconnected, and the extracorporeal system cleaned. Cleaning can include sanitization or replacement of the biochemical reactor and readying the system for use by another patient (step 208).

In one embodiment of the device, system, or method of FIGS. 1 and 2, withdrawal of fluids from a human or animal patient can include blood drawn by venipuncture or arterial taps. Other bodily fluids such as cerebrospinal fluid, lymph fluid, urine, stomach, and GI tract fluids can also be processed using the described systems and methods.

In one embodiment of the device, system, or method of FIGS. 1 and 2, the pump can include continuous, intermittent, or variable speed pumps. These can include but are not limited to peristaltic pump systems.

In one embodiment of the device, system, or method of FIGS. 1 and 2, the inlet and outlet can include luer locks or locking cannula systems.

In one embodiment of the device, system, or method of FIGS. 1 and 2, biochemical reactor can include fluid flow structures such as tubing, capillary tubes, hollow fibers, porous structures, and chambers containing unattached polymer or magnetic beads. Flow structures can be formed in whole or in part from glass, metal, ceramic, or polymeric materials. Fluid flow structures can be continuous, split into multiple separate flow channels using a manifold, or contain circulating closed chamber structures.

In one embodiment of the device, system, or method of FIGS. 1 and 2, immobilized enzymatic biologic agents can include DNase 1, an enzyme with specificities that can catalyze hydrolysis of phosphodiester linkages in the DNA backbone, thus degrading cirDNA and NET-DNA in the blood of a patient. Under biological conditions, DNase 1 can hydrolyze and thereby remove DNA and DNA fragments to disrupt the metastasis process.

In another embodiment, various types of nucleases can be used, including but not limited to human or animal derived endonuclease enzymes including DNase 1, bovine pancreas DNase 1, recombinant bovine pancreas DNase 1, RNase A, and staphylococcal nuclease. Endonuclease enzymes 'break' the cancer-derived DNA and RNA, thereby making these oncogenic nucleic acids unable to initiate cancer at another site in the body.

In one embodiment of the device, system, or method of FIGS. 1 and 2, attachment of enzymatic biologic agents such as DNase 1 can include linkage using conventional affinity tag binding, attachment or adsorption on glass, beads, alginate structures or other matrix, entrapment in insoluble beads or microspheres, and enzymatic cross linkage to create an enzymatically reactive surface, or covalent bonding. Covalent bonding can be random or site specific. Amino, thiol, carboxyl, cyanogen bromide, or metaperiodate activation can be used. In some embodiments, discrete linking agents that are attached between the DNase 1 and a surface can be used. In some embodiments, surfaces can be chemically modified to allow enzyme attachment, or functional groups exposed on the surface can be activated. Covalent or ionic coupling a linking agent or enzyme to the surface can include linking of one or more functional groups on the surface or the enzyme.

In one embodiment of the device, system, or method of FIGS. 1 and 2, biologic agents or compounds that interact with the immobilized enzymatic agents can include blood or fluid conveyed cirDNA. More specifically, in other embodiments, at least one of metastatic cirDNA or cirDNA fragments, NET-DNA, viral cirDNA, and microbial cirDNA can be hydrolyzed after interaction with immobilized endonuclease enzymes including DNase 1.

In one embodiment of the device, system, or method of FIGS. 1 and 2, treatable diseases, conditions, or symptoms of humans or animals can include but are not limited to:
1) Stand-alone treatment or in conjunction with other treatment strategies for brain cancer (such as glioblastoma), nerve cancer (such as Schwannomas and neurofibrosarcoma), sarcomas that develop from connective tissues including muscle, fat, and blood vessels, breast cancer, lung cancer, bone cancer, liver cancer, esophageal cancer, pancreatic cancer, stomach cancer, intestinal cancer, colorectal cancer, kidney cancer, bladder cancer, prostate cancer, uterine cancer, testis cancer, ovarian cancer, cardiac cancer, and skin cancers including malignant melanoma.

2) Prophylactic treatment of the blood of a patient after detection of a solid tumor;
3) Prophylactic treatment of the blood of a patient after detection of abnormally high cirDNA that may suggest metastasis of a solid tumor with a concurrent decrease in DNase levels in the blood of a patient;
4) Palliative treatment of the blood of a patient after detection of metastatic cirDNA from one or more tumors;
5) Treatment of the blood of a patient after surgery (e.g., surgical stress) or beginning chemotherapy which may cause an increase in apoptosis or necrosis of tumor cells with accompanying release of cancer DNA into the bloodstream of the patient;
6) Treatment of the blood of a patient to abrogate metastases due to NET-DNA and cirDNA associated with cell fragments released from living and dying tumor cells;
7) Treatment of the blood of a patient due to bacterial, yeast, fungal, or viral infections that result in increased levels of cirDNA in the bloodstream of a patient; and
8) Treatment of the blood of a patient to reduce levels of proinflammatory compounds, such as DNA, in the bloodstream that may be elevated following a course of systemic antibiotic treatment and chemotherapy.

Figure 3:
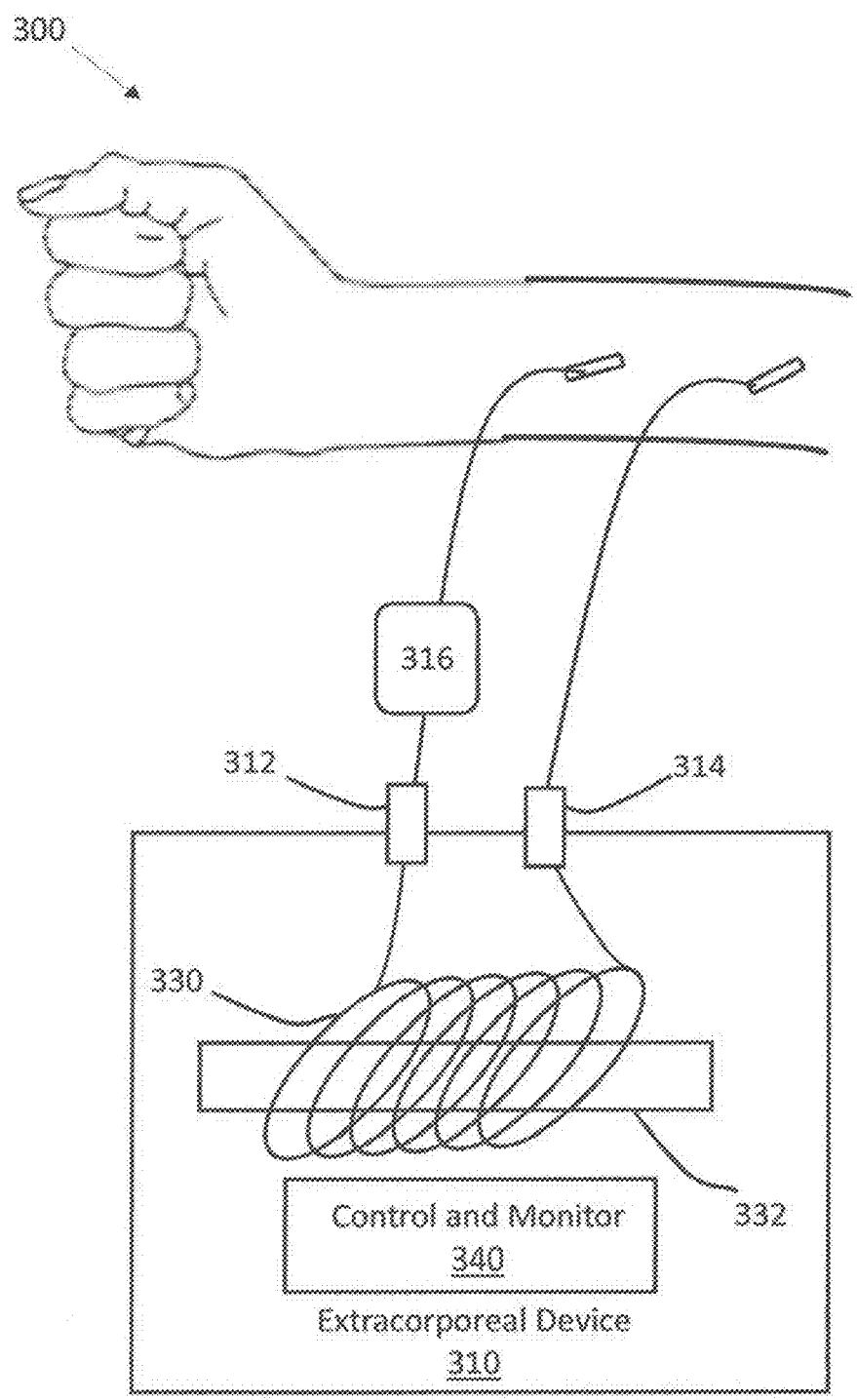
FIG. 3 illustrates one embodiment of an extracorporeal device that can be attached to receive and treat blood that includes coiled tubing supporting immobilized enzymes.

FIG. 3 illustrates one embodiment of an extracorporeal device that can be attached to receive and remove cirDNA in blood that includes coiled tubing supporting immobilized enzymes. As seen in FIG. 3, a system 300 can be attached to receive blood from vein connections to a patient's arm. The system 300 includes an extracorporeal device 310 having a luer lock inlet 312 and luer lock outlet 314. Using a fluid pump 316, blood or other fluid is introduced and passed through a replaceable biochemical reactor 330 that includes coiled or otherwise compactified tubing. Surface attached and immobilized enzymatic agents in the biochemical reactor can remove cirDNA or other undesired contaminants and return the processed blood to the patient using outlet 314. A control and monitoring system 340 can be used to set fluid flow rates, maintain, and monitor fluid temperature, and support sensors that can determine efficacy of cirDNA destruction. In this embodiment, a heater element 332 can be connected to the control and monitor device to maintain blood temperature at about 37 degrees Celsius for human patients, or normal blood temperature for non-human patients.

Figure 4:
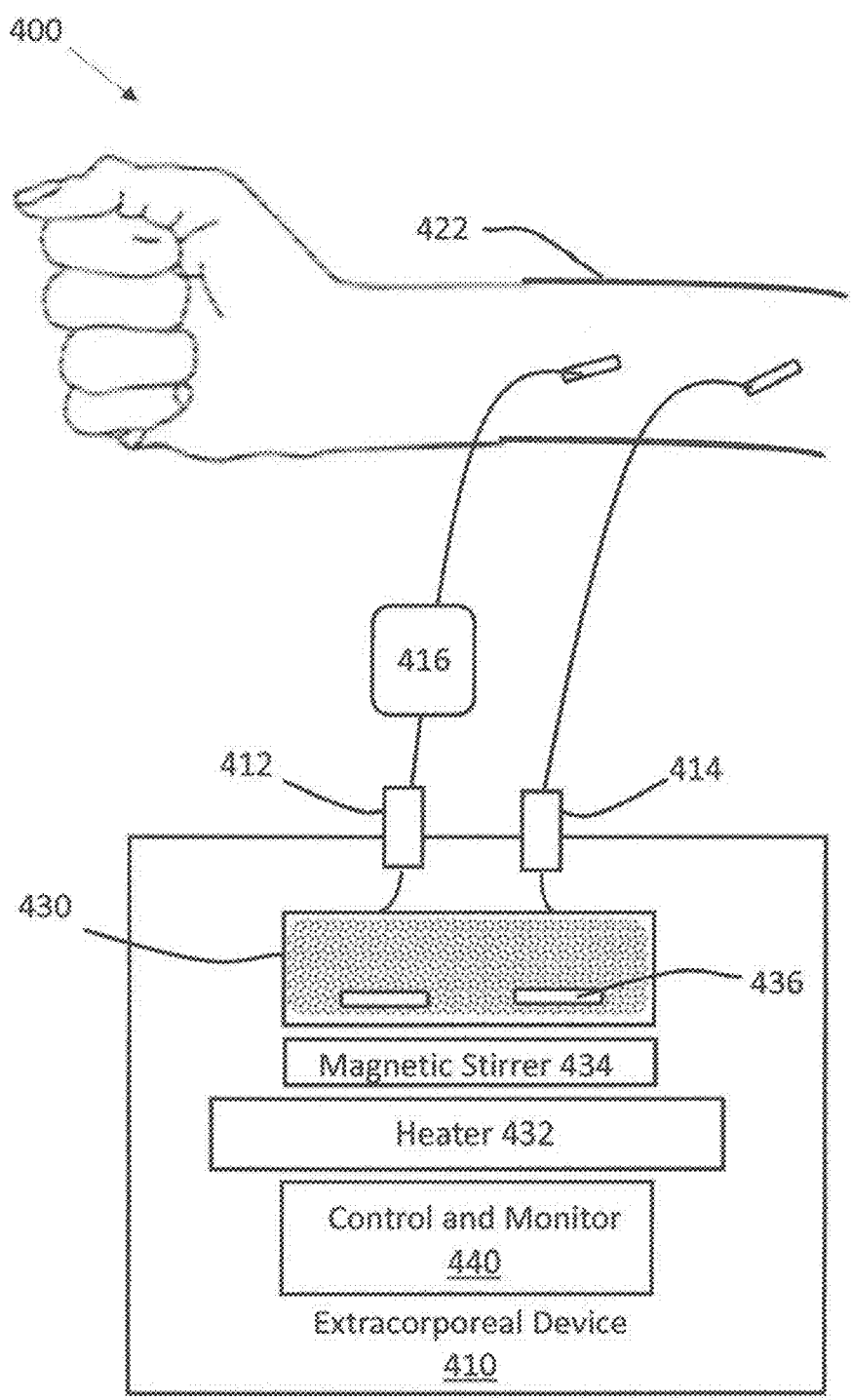
FIG. 4 illustrates one embodiment of an extracorporeal device that can be attached to receive and treat blood that includes a flow chamber supporting beads with immobilized enzymes.

FIG. 4 illustrates one embodiment of an extracorporeal device that can be attached to receive and remove cirDNA in blood that includes a flow chamber supporting beads with immobilized enzymes. As seen in FIG. 4, a system 400 can be attached to receive blood or other fluids from arteries or vein connections to a patient's arm. The system 400 includes an extracorporeal device 410 having a luer lock inlet 412 and luer lock outlet 414. Using a fluid pump 416, blood or other fluid is introduced and passed through a replaceable biochemical reactor 430 that includes a fluid chamber partially filled with beads having surface attachment with immobilized enzymatic agents. A magnetic stirring system 434 can be used to rotate magnetic cylinders 436 within the replaceable biochemical reactor 430. Surface attached and immobilized enzymatic agents in the biochemical reactor can remove cirDNA or other undesired nucleic acids and return the processed blood to the patient using outlet 414. A control and monitoring system 440 can be used to set fluid flow rates, maintain, and monitor fluid temperature, and support sensors that can determine efficacy of cirDNA destruction. In this embodiment, a heater element 432 can be connected to the control and monitor device to maintain blood temperature at a desired set point.

Figure 5:
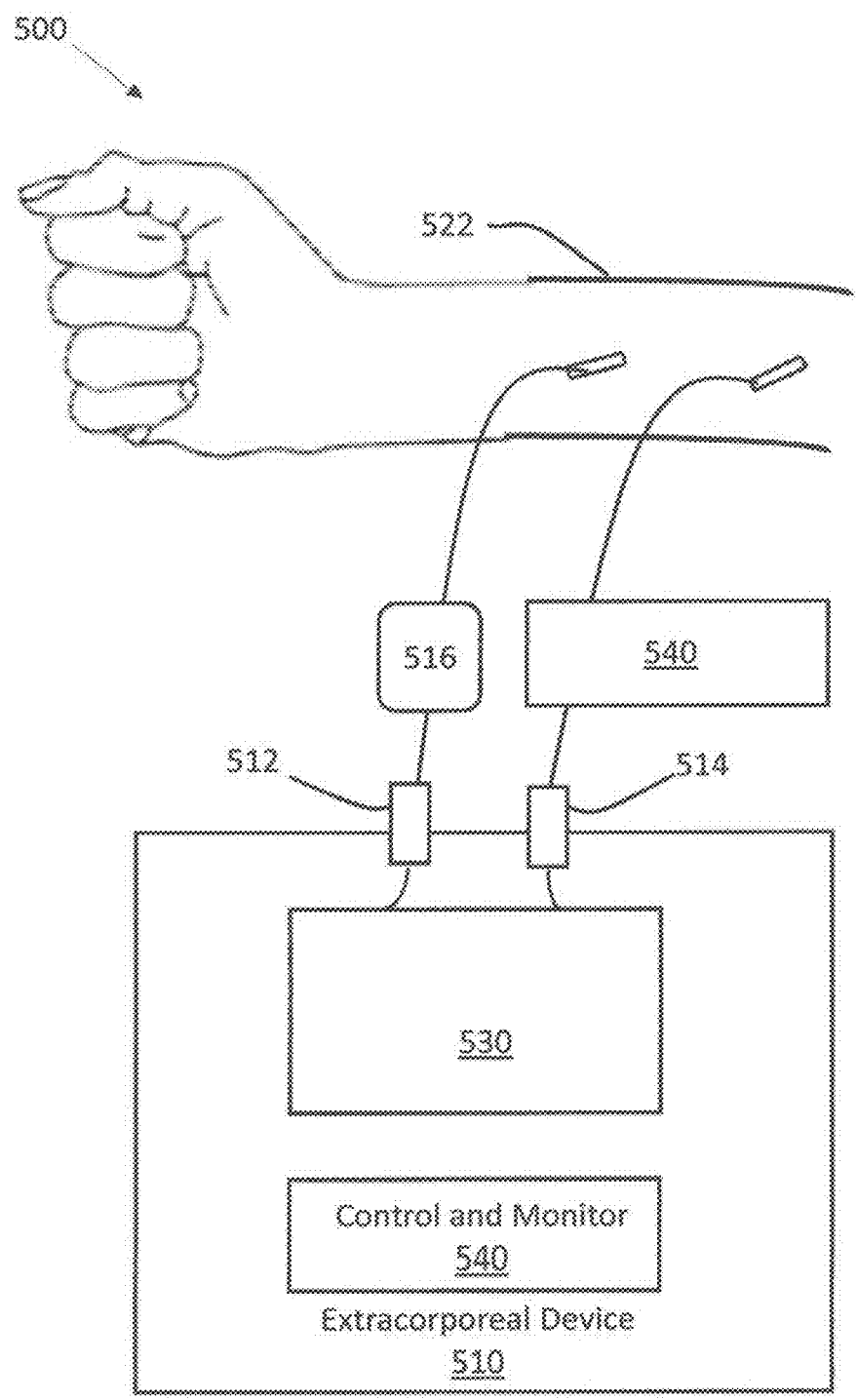
FIG. 5 illustrates one embodiment of an extracorporeal device that can be attached to receive and treat blood that is further connected to other diagnostic or therapeutic equipment.

FIG. 5 illustrates one embodiment of an extracorporeal device that can be attached to receive and treat blood that is further connected to other diagnostic or therapeutic equipment. As seen in FIG. 5, a system 500 can be attached to receive blood or other fluids from arteries or vein connections to a patient's arm. The system 500 includes an extracorporeal device 510 having a luer lock inlet 512 and luer lock outlet 514. Using a fluid pump 516, blood or other fluid is introduced and passed through a replaceable biochemical reactor 530 that includes immobilized enzymatic agents such as DNase 1. After passing through the biochemical reactor 530, blood can be further processed by separate (as shown) or built-in diagnostic or therapeutic systems 540. Diagnostic systems can include inline assays for DNA (e.g., absorbance at 260 nm or fluorometric assay using excitation at 651 nm and emission at 681 nm), real-time flow cytometry, or other blood health diagnostics. Therapeutic systems can include additional hemoperfusion, hemofiltration, oxygenation, or other blood processing methods, such as those that may use a separate biochemical reactor from the biochemical reactor 530. In some embodiments, diagnostic or therapeutic systems 540 can include in-line sampling ports that permit periodic sample taking.

Figure 6:
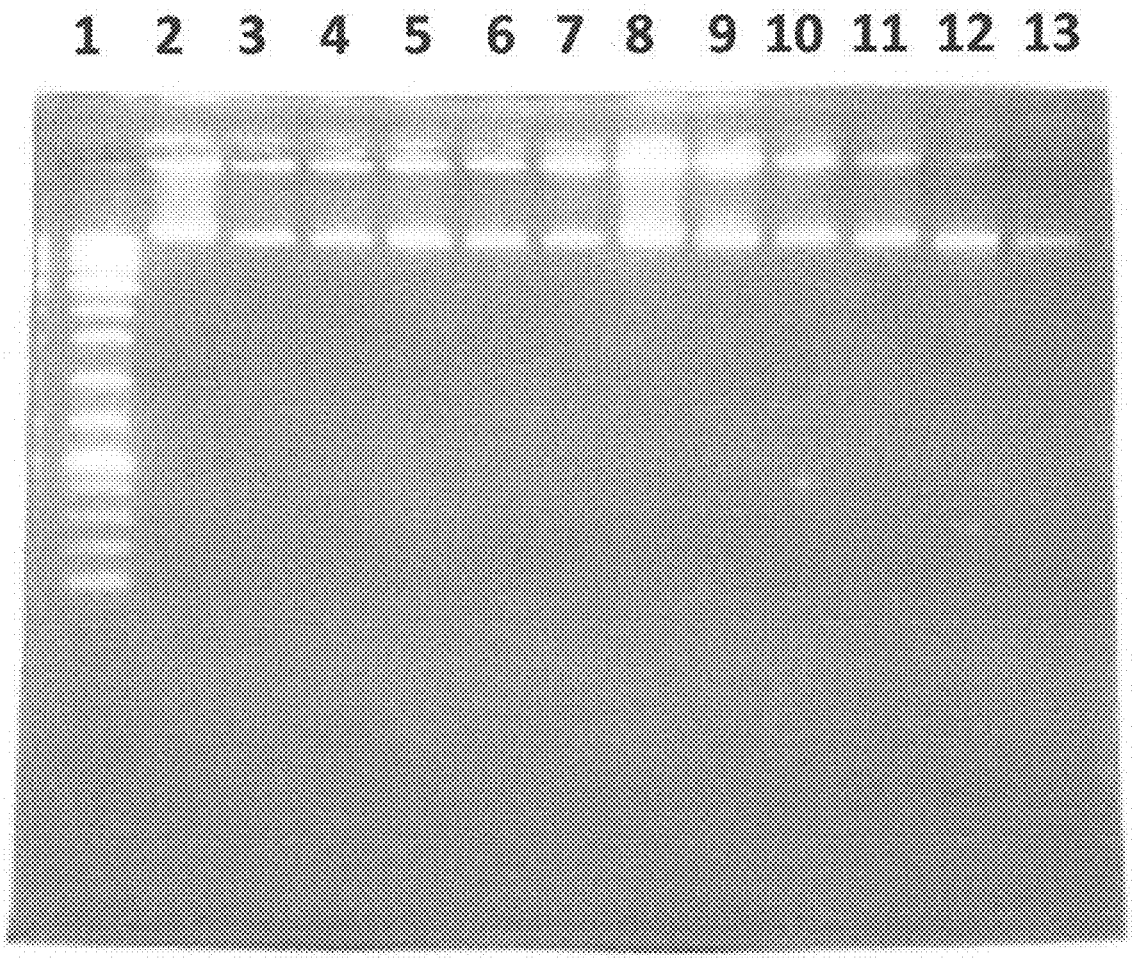
FIG. 6 illustrates an agarose gel following electrophoresis and ethidium bromide staining to reveal destruction of HeLa genomic DNA (gDNA) with DNase 1 immobilized on agarose microbeads after incubation in vitro in an aqueous buffer at pH 7.4 for 150 minutes (lanes 8-13)

FIG. 6 illustrates the in vitro use of a biochemical reactor containing immobilized DNase 1 agarose beads (50 µl of 1.6 mg DNase 1 per ml resin) in a column. The 125 ng/µl HeLa cell gDNA in a buffer system containing 50 mM (N,N-bis (2-hydroxyethyl)-2-aminoethanesulfonic acid (BES), 2 mM $CaCl_2$), and 2.5 mM $MgCl_2$ at pH 7.4 (BES buffer) was passed from the from the gDNA reservoir, through the column at a flow rate of 0.12 ml/min at room temperature and was recirculated back to the reservoir. Samples were collected from the reservoir initially, and at 30 minute intervals for 150 minutes. The samples at each time point and samples for the controls at each time point were loaded onto 1.5% agarose gel, and electrophoresis was run at 100 V. The destruction of the cancer cell DNA was determined by fluorescence plate liquid chromatography (FPLC) of samples taken at each time point followed by ethidium bromide staining and densitometry readings by pixel counts of DNA bands in the agarose gel. There was about 90% destruction of the HeLa gDNA at 150 minutes in this experiment, which demonstrated that DNase 1 immobilized on agarose microbeads in a biochemical reactor rapidly destroys cancer DNA. There was no measurable destruction of DNA in the control in which the gDNA in BES buffer was recirculated through a column containing agarose microbeads without DNase 1.

Figure 7:
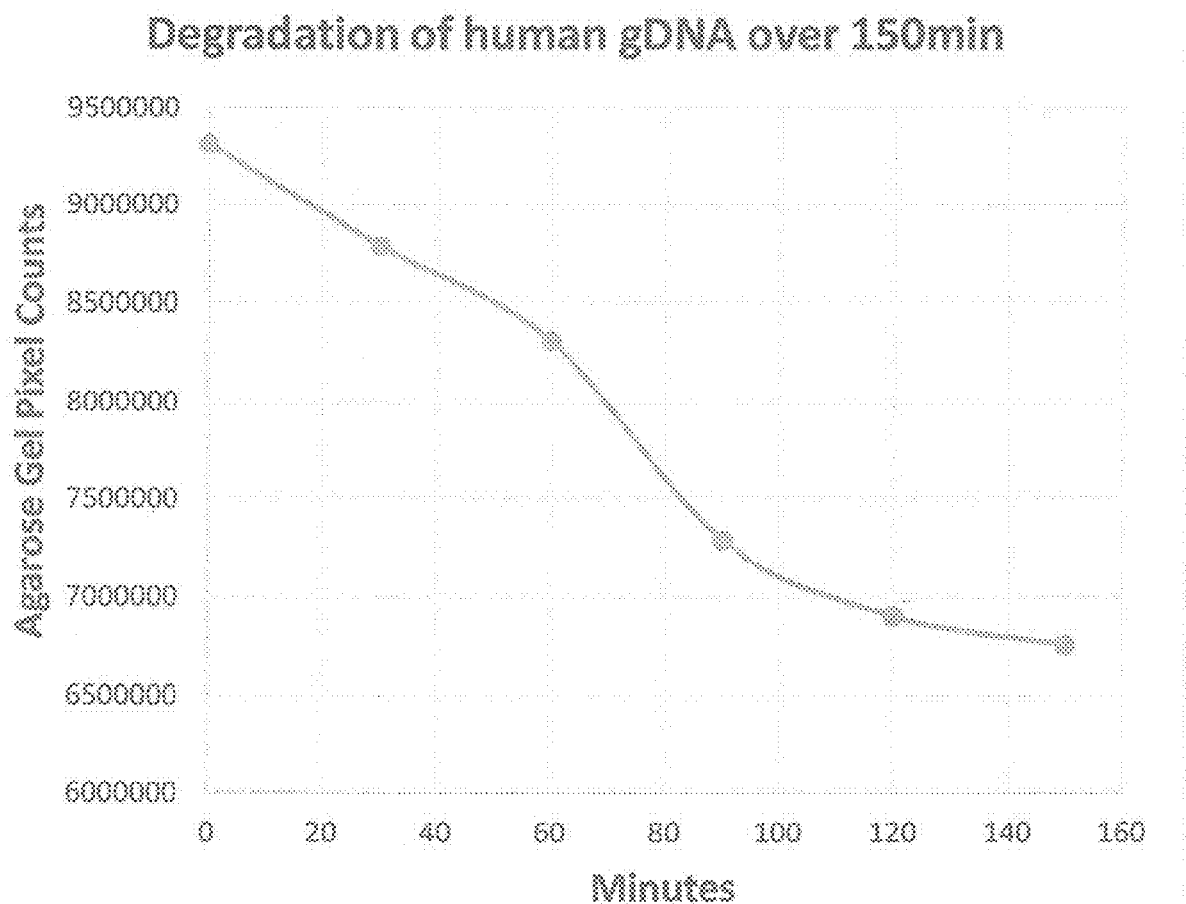
FIG. 7 illustrates the destruction of HeLa cell gDNA in vitro based on image densities of stained gDNA in lanes 8-13 of the agarose gel shown in FIG. 6.

FIG. 7 illustrates the destruction of 125 ng/µl HeLa gDNA following incubation for 150 minutes at room temperature with DNase 1 on Agarose beads using image densities of stained gDNA shown in FIG. 6. FIGS. 6 and 7 demonstrate that DNase 1 immobilized on agarose microbeads in the biochemical reactor destroys cancer DNA.

Various modifications to the foregoing described embodiments can be made. For example, multiple glass or plastic capillary tubing reaction chambers can be connected in series to act as biochemical reactors. In one embodiment, a first capillary tubing can contain immobilized DNase 1 to hydrolyze metastatic cirDNA and a second capillary tubing that contains immobilized alkaline phosphatase enzymes including SBAP and/or apyrase to dephosphorylate the cirDNA, NET-DNA, and DNA fragments to reduce the likelihood of attachment of the cirDNA and DNA fragments to cellular receptors, and to dephosphorylate extracellular adenosine diphosphate (eADP) to reduce activation of platelets and the blood clotting process that may interfere with continued optimum activity of DNase 1 and phosphatase enzymes in the biochemical reactor. In other embodiments, a replaceable biochemical reactor can be used. The replaceable biochemical reactor can include immobilized DNase 1 or other nuclease enzymes covalently attached to magnetic microbeads that are held by magnetic attraction to the inner surface of capillary tube. In still other embodiments magnetic microbeads with covalently attached enzymatic agents including DNase 1 and RNase A enzymes can be used in conjunction with a magnetic stirring system that is used to rotate magnetic cylinders within the biochemical reactor. Stirring cylinders can include surface attached and immobilized enzymatic agents to destroy metastatic cirDNA, nucleic acids, and nucleotides in the blood of the patient as the blood is pumped continuously through the biochemical reactor.

Although immobilized DNase 1 may not be able to hydrolyze DNA within cancer cells that are released into the bloodstream from a solid tumor, shearing forces acting on these cells as they move through blood vessels and capillaries may rupture these cells, and the metastatic cancer cells may be destroyed by the host immune system, which would release the cancer mitochondrial DNA and gDNA into the bloodstream, so that this metastatic DNA could be destroyed as the blood of the patient is pumped continuously through the biochemical reactor.

As will be appreciated, the described systems and methods of FIGS. 3, 4, and 5 that are applicable to venous blood taken and returned to a patient arm can be adapted to process fluids from other body sites. Such bodily fluids may be routed to the extracorporeal device for treatment to remove metastatic cirDNA and NET-DNA and then returned to the body.

In addition to DNase 1 enzymes previously discussed, other endonuclease and phosphodiesterase enzymes including any of human DNase 1, RNase, any of synthetic or man-made DNase, such as DNase 1 made from recombinant DNA including *Escherichia coli*, or RNase, any animal phosphodiesterase including DNase and RNase enzymes, and any natural or synthetic bacterial, yeast, fungal, algal, plant, or protozoan phosphodiesterase or endonuclease enzymes, such as neurospora nuclease or mung bean nuclease, can be used. Advantageously, it may be possible to perform a liquid biopsy on the blood of the patient, harvest the DNase 1 contained therein, immobilize this DNase 1 in a biochemical reactor comprised of microbeads (e.g., Agarose) or the inner surface of capillary tubing, so that the DNase 1 is the patient's DNase 1, which would avoid the possibility of adverse immunological responses or platelet activation and blood clotting as a result of contact with a 'foreign' enzyme in the bloodstream. If it appears unfeasible to obtain enough of the patient's DNase 1 by use of liquid biopsy, the patient's DNase 1 could be synthesized by use of recombinant DNA technologies, immobilized, and used in a biochemical reactor, as described above.

In some embodiments, an extracorporeal device with attached DNase 1 in the biochemical reactor can be used as a stand-alone device or in conjunction with other treatment modalities. This can include but is not limited to devices or treatments including fluid replacement, corticosteroids, oral and IV administration of antibiotics and chemotherapeutic agents, for reduction of metastatic cirDNA or RNA released from tumors and bystander cells that undergo apoptosis or necrosis to release DNA and RNA, and viral nucleic acids in a patient's blood, such as discussed herein, are also contemplated. More specifically, treatment of the blood of a patient may be done as a stand-alone therapy or in conjunction with other cancer treatments including use of alkaline phosphatase, and specifically SBAP or apyrase, in an extracorporeal device similar to the extracorporeal deice for DNase 1 described herein, so that cirDNA may be broken into non-cancerous nucleotide fragments as a result of action of DNase 1, and both cirDNA and DNA fragments may be dephosphorylated as a result of action of the SBAP and other phosphatase enzymes (16), so that the cirDNA and DNA fragments are unable to attach to cellular recognition sites to initiate inflammatory reactions.

Example 1

In one example embodiment, a sterile hypodermic needle set can be used for accessing a patient's vein, (e.g., Blood Collection Set, Vaculet 21G×¾" Winged, w/Multi-Sample Adapter, 12" Tubing, or similar vein accessing device with a larger bore needle, if needed). A 36" length of sterile plastic tubing can be used to pass through a peristaltic pump and connect the Vaculet with the biochemical reactor with a luer lock. The peristaltic pump or similar pumping device can be used for pumping blood from the patients arm to the biochemical reactor.

An external continuous-flow biochemical reactor is prepared by immobilizing DNase 1 on the inner surface of polystyrene, polymethacrylate, or other plastic capillary tubing as described by Habja and Guttman "Continuous-flow biochemical reactors: Biocatalysis, bioconversion, and bioanalytical applications using immobilized microfluidic enzyme reactors". J. Flow. Chem. 6(1):8-12, 2015, or Mohamad, et al. "An overview of technologies for immobilization of enzymes and surface analysis techniques for immobilized enzymes. Biotech. Biotechnol. Equip. 29(2): 205-220, 2015. Enough capillary tubing (i.e., preferably up to 36 inches long) is used to allow immobilization of 50-1,500 IU DNase 1, and preferably 200-1,000 IU DNase 1 in the tubing, which becomes the biochemical reactor. The plastic tubing with immobilized DNase 1 on the inner surface is sterilized and may be stored in the refrigerator at 4° C. for several months prior to use. When ready for use, the plastic tubing is placed into a 12"×12"×12" chamber that has a lid that opens for placement of the tubing inside, a side opening with a luer lock for connection to the plastic tubing from the patient's arm (by way of the peristaltic pump), and a second side opening with a luer lock for connecting to the line that returns blood to the patient. Alternatively, the plastic tubing can be used without insertion into a chamber, with the pump and tubing together forming a portion of the extracorporeal device by themselves. The continuous-flow biochemical reactor can hydrolyze approximately 50% of the cirDNA in blood per passage through it as the blood is pumped slowly (e.g., flow rate of 0.5-50 mL/min, and typically up to 10 mL/min) through the capillary tubing before returning it to the patient. Passage of the patient's blood through the biochemical reactor hydrolyzes the metastatic cirDNA in the patient's blood before it is returned to the patient, thereby abrogating metastasis of the primary tumor DNA to sites in the body that are distant from the primary tumor.

Example 2

A sterile hypodermic needle set can be used for accessing a patient's vein and a peristaltic pump can be used for pumping blood from the patients arm to a biochemical reactor. An external continuous-flow biochemical reactor is prepared by use of a sterile 250 mL closed container with a magnetic stirring bar that contains 10-150 g, and preferably 50 g of microbeads with immobilized DNase 1, prepared by covalent bonding to have 50-1,500 IU DNase 1, and preferably 200-1,000 IU DNase 1 prepared aseptically in the biochemical reactor. The external continuous-flow biochemical reactor has inlet and outlet connections for connecting with blood being pumped to and from the continuous-flow biochemical reactor. The container with DNase 1 covalently immobilized on the plastic beads is sterilized and may be stored in the refrigerator at 4° C. for several months prior to use. When ready for use, the container is placed onto a magnetic stirrer and stirring is started when blood begins to fill the container. A length of sterile plastic tubing is used to connect the biochemical reactor to the patient's arm vein for returning treated blood to the patient's arm or leg vein.

The peristaltic pump may be turned on after checking to ensure that all connections are tight so that they will not leak or allow the blood to become contaminated, and the pump is run continuously. Passage of the patient's blood through the biochemical reactor hydrolyzes and thereby destroys metastatic cirDNA and NET-DNA in the patient's blood before it is returned to the patient.

The biochemical reactor chamber is maintained at approximately body temperature (37° C.) by use of a thermostatically-controlled heating device. The patient's blood is pumped continuously through the biochemical reactor until analytical testing shows that levels of the cirDNA have been reduced to undetectable or baseline levels and the patient's signs have returned to normal.

Example 3

This example illustrates the in vitro use of a biochemical reactor containing immobilized DNase 1 agarose beads (100 µl of 1.6 mg DNase 1 per ml resin) in a column though which HeLa cell gDNA in (N,N-bis(2-hydroxyethyl)-2-aminoethanesulfonic acid) (BES) buffer containing 50 mM BES, 2 mM $CaCl_2$), and 2.5 mM $MgCl_2$ at pH 7.5 (BES buffer) is passed from the from the DNA reservoir, through the column at a flow rate of 1 ml/min, and recirculated back to the reservoir. Samples were collected from the reservoir initially, and at 5 minute intervals for 30 minutes. The destruction of the cancer cell DNA was determined by fluorescence plate liquid chromatography (FPLC) of samples taken at each time point followed by ethidium bromide staining and densitometry readings by pixel counts of DNA bands in the agarose gel in FIG. 6. There was about 90% destruction of the HeLa cancer cell gDNA within 150 minutes in this experiment, which is illustrated in FIG. 7.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

REFERENCES

1. Massague, J, E. Batlle and R. R. Gomis. Understanding the molecular mechanisms driving metastasis. *Molecular Oncology* 11:3-4 (2017).
2. Garcia-Olmo, G. et al. Horizontal transfer of DNA and the "genometastasis hypothesis". *Blood* 95(2):724-725 (2000).
3. Thierry, A. R. et al. Origins, structures, and functions of circulating DNA in oncology. *Cancer Metastasis Rev.* 35:347-376 (2016).
4. Garcia-Olmo, G. et al. Quantitation of cell-free DNA and RNA in plasma during tumor progression in rats. *Molecular Cancer* 12(8):1-10 (2013).
5. Lo, K. W., et al. Analysis of cell-free Epstein-Barr virus associated RNA in the plasma of patients with nasopharyngeal carcinoma. *Clin. Chem.* 45:1292-1294 (1999).
6. Kopreski, M. S., et al. Detection of tumor messenger RNA in the serum of patients with malignant melanoma. *Clin. Cancer. Res.* 5:1961-1965 (1999).
7. Alekseeva, L. A., et al. Targeting circulating SINEs and LINEs with DNase 1 provides metastases inhibition in experimental tumor models. *Molecular Therapy: Nucleic Acids* 20:50-61 (2020).
8. Patulina, O. A. et al. Tumoricidal activity of RNase and DNase 1. *Acta Naturare* 2 No. 1(4):88-93 (2010).
9. Tamkovich, S. N., et al. Circulating DNA and DNase activity in human blood. *Ann. N.Y. Acad. Sci.* 1075:191-196 (2006).
10. Fleischhacker, M. and B. Schmidt. Pre-analytical issues in liquid biopsy—where do we stand? *J. Lab Med.* 44(3):117-142 (2020).
11. Park, J., et al. Cancer cells induce metastasis-supporting neutrophil extracellular DNA traps. *Sci. Transl. Med.* 8:(361ra138), 1-12 (2016).
12. Kolaczkowska, E., et al. Molecular mechanisms of NET formation degradation revealed by intravital imaging in the liver vasculature. *Nat. Commun.* 6(6673):1-13 (2015).
13. Cools-Lartigue, J., et al. Neutrophil extracellular traps sequester circulating tumor cells and promote metastasis. *J. Clin. Invest.* 123:3446-3458 (2013).
14. Tohme, S., et al. Neutrophil extracellular traps promote the development and progression of liver metastases after surgical stress. *Cancer Res.* 76:1367-1380 (2016).
15. Yang, L., et al. DNA of neutrophil extracellular traps promotes cancer metastasis via CCDC25. *Nature* 583 (7814):133-138 (2020).
16. Orth, D. S. Blood Processing Apparatus and Method for Detoxifying Bacterial Lipopolysaccharide. U.S. Pat. No. 10,881,781, Jan. 5, 2021.

The invention claimed is:

1. A blood treatment method, comprising:
   inducing flow of blood of a patient through an extracorporeal device inlet and outlet to a circulatory system of the patient; and
   destroying metastatic agents contained within the blood of the patient by continuously passing the blood of the patient over a biochemical reactor surface having attached deoxyribonuclease 1 (DNase 1) enzyme, with the biochemical reactor surface being contained within the extracorporeal device;
   wherein the DNase 1 enzyme comprises human DNase 1 from human blood or tissues or synthetic human DNase 1 from recombinant deoxyribonucleic acid (DNA) technology;
   wherein the DNase 1 enzyme is immobilized and is used prophylactically or therapeutically to remove selected nucleic acids within a biological system, including but not limited to those produced by cancer cells in humans and animals, and more specifically, removal of cancer metastases including tumor cells, and metastatic DNA including circulating DNA (cirDNA) and neutrophil extracellular trap DNA (NET-DNA) in a bloodstream of the patient by passage of the blood of the patient through the extracorporeal device and over the biochemical reactor surface, without adding any chemicals to the blood of the patient, and returning the blood of the patient to the patient for continuous treatment until the metastatic DNA has been reduced to predetermined or undetectable levels.

2. The blood treatment method of claim 1, wherein the DNase 1 enzyme destroys metastatic DNA in the blood of the patient.

3. The blood treatment method of claim 1, wherein the metastatic DNA includes any of:
   metastatic circulating DNA (cirDNA) in the blood of the patient;
   metastatic nuclear and mitochondrial cirDNA in the blood of the patient;
   metastatic neutrophil extracellular trap DNA (NET-DNA) in the blood of the patient;
   metastatic cirDNA complexed with serum proteins in the blood of the patient; and
   metastatic DNA from a tumor complexed with cell-free membrane constituents.

4. The blood treatment method of claim 1, wherein the DNase 1 enzyme destroys the metastatic DNA contained within the blood of the patient by hydrolytic cleavage of phosphodiester linkages within polynucleotide chains of the metastatic DNA.

5. The blood treatment method of claim 1, wherein hydrolyzing the metastatic DNA in the blood of the patient is used to therapeutically prevent metastasis of cancer including at least one of brain cancer, glioblastoma, blood and bone marrow cancers including leukemia, lymphoma and myeloma, nerve cancer, Schwannomas, neurofibrosarcoma, sarcomas of connective tissues, sarcomas of nerves, muscles, joints, bone, fat, and blood vessels, breast cancer, lung cancer, bone cancer, liver cancer, esophageal cancer, pancreatic cancer, stomach cancer, intestinal cancer, colorectal cancer, kidney cancer, bladder cancer, prostate cancer, uterine cancer, testis cancer, ovarian cancer, cardiac cancer, and skin cancers including malignant melanoma.

6. The blood treatment method of claim 1, wherein the DNase 1 enzyme is covalently attached to the biochemical reactor surface.

7. The blood treatment method of claim 1, wherein the biochemical reactor surface further comprises at least one of capillary tubing and microbeads.

8. The blood treatment method of claim 1, wherein the biochemical reactor surface comprises magnetic microbeads.

9. The blood treatment method of claim 1, wherein blood is continuously treated.

10. The blood treatment method of claim 1, wherein blood is removed from a patient and batch treated.

11. The blood treatment method of claim 1, further comprising the step of pumping the blood of the patient through the extracorporeal device inlet and outlet in fluid connection to the circulatory system of the patient.

12. The blood treatment method of claim 1, wherein the biochemical reactor surface is provided with a continuous flow of the blood of the patient that continues until the metastatic DNA has been reduced to predetermined or undetectable levels.

13. The blood treatment method of claim 1, wherein the DNase 1 enzyme is obtained by harvesting the DNase 1 enzyme from the blood or tissues of a cancer patient, and immobilizing the DNase 1 enzyme onto the biochemical reactor surface.

14. The blood treatment method of claim 13, wherein the DNase 1 enzyme is used prophylactically to treat blood of a cancer patient following surgery, microbial infection, sepsis, and chemotherapy to prevent cancer metastases.

15. The blood treatment method of claim 1, wherein the DNase 1 enzyme is used prophylactically to treat blood of the patient during and following bacterial, yeast, fungal, or viral infections that may result in increased levels of circulating DNA (cirDNA) in the bloodstream of the patient.

16. The blood treatment method of claim 1, wherein the DNase 1 enzyme is immobilized and is used to therapeutically treat any metastatic cancer as a stand-alone treatment or in conjunction with other cancer treatment therapies including any of:
   Immobilized enzymes or antibodies on beads or in capillary columns;
   ribonuclease A (RNase A) immobilized on the biochemical reactor surface with the DNase 1 enzyme;
   RNase A immobilized in a first separate biochemical reactor connected in series with the biochemical reactor surface having the attached DNase 1 enzyme;
   *Saccharomyces boulardii* alkaline phosphatase (SBAP) or apyrase immobilized on the biochemical reactor surface having the attached DNase 1 enzyme;
   SBAP or apyrase immobilized in a second separate biochemical reactor connected in series with the biochemical reactor surface having the attached DNase 1 enzyme;
   Alpha-1 antitrypsin inhibitor (A1AT) immobilized on the biochemical reactor surface having the attached DNase 1 enzyme;
   A1AT immobilized in a third separate biochemical reactor connected in series with the biochemical reactor surface having the attached DNase 1 enzyme;
   Anti-actin immobilized in the biochemical reactor surface having the attached DNase 1 enzyme; and
   Anti-actin immobilized in a fourth separate biochemical reactor connected in series with the biochemical reactor surface having the attached DNase 1 enzyme.

17. A blood treatment system, comprising:
   an extracorporeal device having an inlet and outlet able to be placed in fluid connection to a circulatory system of a patient; and a biochemical reactor surface having attached deoxyribonuclease 1 (DNase 1) enzyme, with the biochemical reactor being contained within the extracorporeal device and acting to remove cancer metastases contained within blood of the patient;

wherein the biochemical reactor surface comprises at least one of capillary tubing and microbeads;

wherein the DNase 1 enzyme is immobilized and is used prophylactically or therapeutically to remove selected nucleic acids within a biological system, including but not limited to those produced by cancer cells in humans and animals, and more specifically, removal of cancer metastases including tumor cells, and metastatic DNA including circulating deoxyribonucleic acid (DNA) (cirDNA) and neutrophil extracellular trap DNA (NET-DNA) in a bloodstream of the patient by passage of the blood of the patient through the extracorporeal device and over the biochemical reactor surface, without adding any chemicals to the blood of the patient, and returning the blood of the patient to the patient for continuous treatment until the metastatic DNA has been reduced to predetermined or undetectable levels.

18. The blood treatment system of claim 17, further comprising a pump arranged to pump the blood of the patient through the extracorporeal device inlet and outlet in fluid connection to the circulatory system of the patient; wherein the DNase 1 enzyme comprises human DNase 1 isolated from blood or tissues of the patient or recombinant human DNase 1.

19. The blood treatment system of claim 17, wherein the DNase 1 enzyme removes metastatic DNA from the blood of the patient.

20. The blood treatment system of claim 17, wherein the metastatic DNA includes any of:

metastatic circulating DNA (cirDNA) in the blood of the patient;

metastatic nuclear and mitochondrial cirDNA in the blood of the patient;

metastatic neutrophil extracellular trap DNA (NET-DNA) in the blood of the patient;

metastatic cirDNA complexed with serum proteins in the blood of the patient; and metastatic DNA from a tumor complexed with cell-free membrane constituents.

21. The blood treatment system of claim 17, wherein the DNase 1 enzyme removes the metastatic DNA, circulating DNA (cirDNA), and neutrophil extracellular trap DNA (NET-DNA) contained within the blood of the patient by hydrolytic cleavage of phosphodiester linkages within polynucleotide chains of this metastatic DNA.

22. The blood treatment system of claim 17, wherein the system is operable to therapeutically treat any metastatic cancer including at least one of brain cancer, glioblastoma, meningioma, blood and bone marrow cancers, leukemia, lymphoma, myeloma, nerve cancer, Schwannomas, neurofibrosarcoma, sarcomas of connective tissues, sarcomas of nerves, muscles, joints, bone, fat, and blood vessels, breast cancer, lung cancer, bone cancer, liver cancer, esophageal cancer, pancreatic cancer, stomach cancer, intestinal cancer, colorectal cancer, kidney cancer, bladder cancer, prostate cancer, uterine cancer, testis cancer, ovarian cancer, cardiac cancer, and skin cancers including malignant melanoma.

23. The blood treatment system of claim 17, wherein the DNase 1 enzyme is covalently attached to the biochemical reactor surface.

24. The blood treatment system of claim 17, wherein the biochemical reactor surface is arranged to receive a continuous blood flow from the patient that continues until the metastatic DNA has been reduced to predetermined or undetectable levels.

\* \* \* \* \*